United States Patent
Nakamura et al.

(10) Patent No.: US 11,197,363 B2
(45) Date of Patent: Dec. 7, 2021

(54) X-RAY TUBE DEVICE

(71) Applicant: FUJIFILM Corporation, Tokyo (JP)

(72) Inventors: Kenji Nakamura, Kanagawa (JP); Ryosuke Ogura, Kanagawa (JP); Keiichiro Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/062,021

(22) Filed: Oct. 2, 2020

(65) Prior Publication Data

US 2021/0029810 A1    Jan. 28, 2021

Related U.S. Application Data

(63) Continuation of application No. PCT/JP2019/014811, filed on Apr. 3, 2019.

(30) Foreign Application Priority Data

Apr. 5, 2018  (JP) .............................. JP2018-073485

(51) Int. Cl.
*H05G 1/06* (2006.01)
*A61B 6/00* (2006.01)

(52) U.S. Cl.
CPC .................. *H05G 1/06* (2013.01); *A61B 6/40* (2013.01); *A61B 6/4405* (2013.01)

(58) Field of Classification Search
CPC ............ H05G 1/06; A61B 6/40; A61B 6/4405
See application file for complete search history.

(56) References Cited

U.S. PATENT DOCUMENTS

| | | | |
|---|---|---|---|
| 2006/0098779 A1 | 5/2006 | Turner | |
| 2013/0230142 A1 | 9/2013 | Murata et al. | |
| 2014/0133627 A1 | 5/2014 | Sakuragi et al. | |
| 2016/0287194 A1 | 10/2016 | Nariyuki et al. | |
| 2018/0116524 A1 | 5/2018 | Aoshima et al. | |
| 2018/0184990 A1* | 7/2018 | Shin ....................... | A61B 6/145 |

(Continued)

FOREIGN PATENT DOCUMENTS

| | | |
|---|---|---|
| JP | 2011-253727 A | 12/2011 |
| JP | 2013-180059 A | 9/2013 |
| JP | 2014-110872 A | 6/2014 |

(Continued)

OTHER PUBLICATIONS

International Search Report dated Jul. 9, 2019 in International Application No. PCT/JP2019/014811.

(Continued)

*Primary Examiner* — Chih-Cheng Kao
(74) *Attorney, Agent, or Firm* — Sughrue Mion, PLLC

(57) ABSTRACT

An X-ray tube device incorporates a mono-tank, and includes a gripping portion that is provided to protrude from a main body in a side surface and supports the main body by gripping. In a case where the main body is divided into two portions of a center-of-gravity-side portion including the center of gravity of the main body and a non-center-of-gravity-side portion not including the center of gravity using a plane passing through the center of the main body and an irradiation direction of X-rays, the gripping portion is in the center-of-gravity-side portion, and the gripping portion is not in the non-center-of-gravity-side portion.

20 Claims, 6 Drawing Sheets

(56) References Cited

U.S. PATENT DOCUMENTS

2019/0015057 A1* 1/2019 Diaz Carmena ......... A61B 6/56

FOREIGN PATENT DOCUMENTS

| JP | 2015-226759 A | 12/2015 |
| JP | 2016-193177 A | 11/2016 |
| JP | 2007-522894 A | 8/2017 |
| WO | 2017/006535 A1 | 1/2017 |

OTHER PUBLICATIONS

Written Opinion of the International Searching Authority dated Jul. 9, 2019 in International Application No. PCT/JP2019/014811.
International Preliminary Report on Patentability dated Oct. 6, 2020 in International Application No. PCT/JP2019/014811.

* cited by examiner

X-RAY TUBE DEVICE

CROSS-REFERENCE TO RELATED APPLICATIONS

This application is a Continuation of PCT International Application No. PCT/JP2019/014811 filed on 3 Apr. 2019, which claims priority under 35 U.S.C § 119(a) to Japanese Patent Application No. 2018-073485 filed on 5 Apr. 2018. The above application is hereby expressly incorporated by reference, in its entirety, into the present application.

BACKGROUND OF THE INVENTION

1. Field of the Invention

The present invention relates to an X-ray tube device.

2. Description of the Related Art

An X-ray tube device may be provided with a gripping portion that is gripped in adjusting a position, an orientation, or the like of the X-ray tube device. In particular, in a portable X-ray tube device, there is an example where, in order to enable the X-ray tube device to be supported by human power during use, gripping portions are provided on both right and left sides of a main body, respectively (WO2017/006535A1, corresponding to US2018/116524A1).

SUMMARY OF THE INVENTION

Since the X-ray tube device incorporates heavy parts, such as a bulb that generates X-rays, normally, it is hard for a user to support the X-ray tube device by gripping one gripping portion. For this reason, the X-ray tube device is supported at two places, such as both sides, to keep a posture. Though not in the X-ray tube device of the related art, in a case where the center of gravity is not at the center of the X-ray tube device, it is particularly hard for the user to support the X-ray tube device by gripping one gripping portion. Accordingly, an object of the invention is to provide an X-ray tube device that allows a user to easily keep a necessary posture by gripping one gripping portion.

An X-ray tube device according to an aspect of the invention comprises a main body that incorporates a mono-tank including a bulb, which generates X-rays, and has a front surface, which is a surface for irradiating the X-rays, a rear surface, which is a surface facing the front surface, and a side surface, which is a surface connecting the front surface and the rear surface, and one gripping portion that is provided to protrude from the main body on the side surface and supports the main body by gripping. In a case where the main body is divided into two portions of the center-of-gravity-side portion including the center of gravity of the main body and a non-center-of-gravity-side portion not including the center of gravity using a plane passing through the center of the main body and an irradiation direction of the X-rays, the gripping portion is in the center-of-gravity-side portion, and the gripping portion is not in the non-center-of-gravity-side portion.

It is preferable that the center of gravity of the main body is at the center between the front surface and the rear surface.

An X-ray tube device according to another aspect of the invention comprises a main body that incorporates a mono-tank including a bulb, which generates X-rays, and has a front surface, which is a surface for irradiating the X-rays, a rear surface, which is a surface facing the front surface, and a side surface, which is a surface connecting the front surface and the rear surface, and one gripping portion that is provided to protrude from the main body on the side surface and supports the main body by gripping. In a case where the main body is divided into two portions of a center-of-gravity-side portion including the center of gravity of the mono-tank and a non-center-of-gravity-side portion not including the center of gravity using a plane passing through the center of the main body and an irradiation direction of the X-rays, the gripping portion is in the center-of-gravity-side portion, and the gripping portion is not in the non-center-of-gravity-side portion.

It is preferable that the center of gravity of the mono-tank is at the center between the front surface and the rear surface.

It is preferable that, in a case where the main body includes a battery, the center of gravity of the battery is in the non-center-of-gravity-side portion.

It is preferable that the center of gravity of the mono-tank, the center of the main body, and the center of gravity of the battery are within the same layer.

It is preferable that the gripping portion is connected to the main body at one place or two places.

It is preferable that the gripping portion and the side surface form a loop shape.

It is preferable that a switch for instructing irradiation of the X-rays is in the non-center-of-gravity-side portion.

It is preferable, in a case where the front surface and the rear surface have a rectangular shape, the gripping portion is provided in the side surface of the main body including short sides of the front surface and the rear surface.

The invention can provide an X-ray tube device that is easily kept in a necessary posture by gripping of one gripping portion.

DESCRIPTION OF THE PREFERRED EMBODIMENTS

First Embodiment

Figure 1:
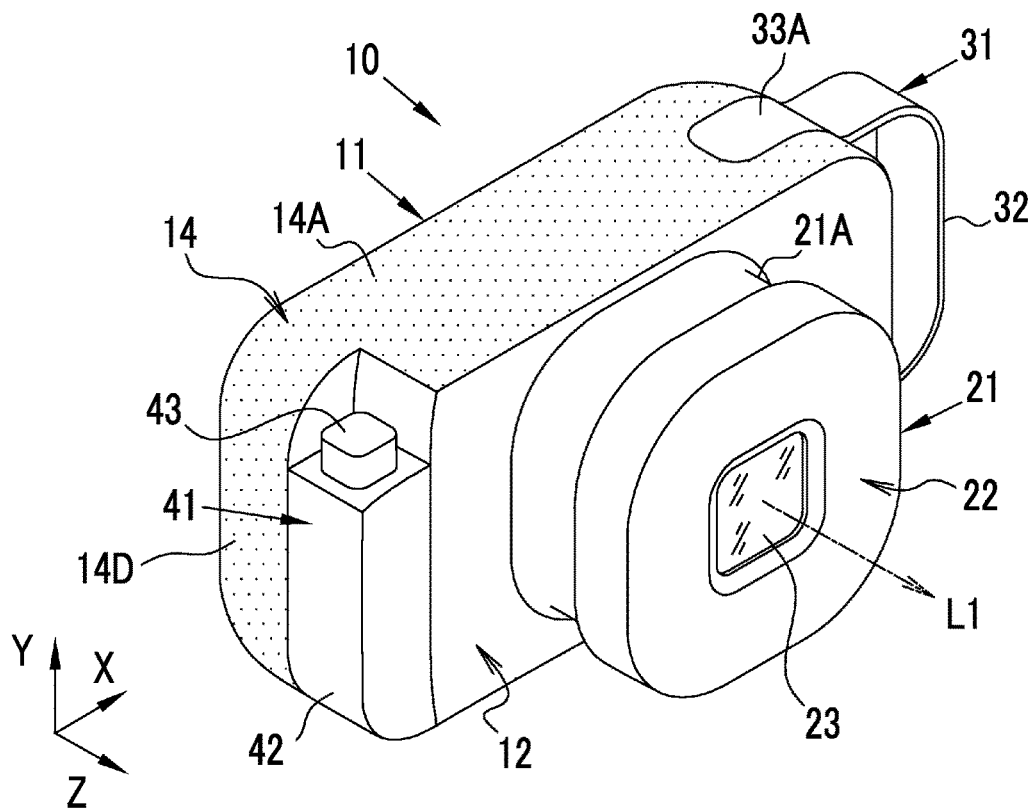
FIG. 1 is a perspective view of an X-ray tube device.
Figure 2:
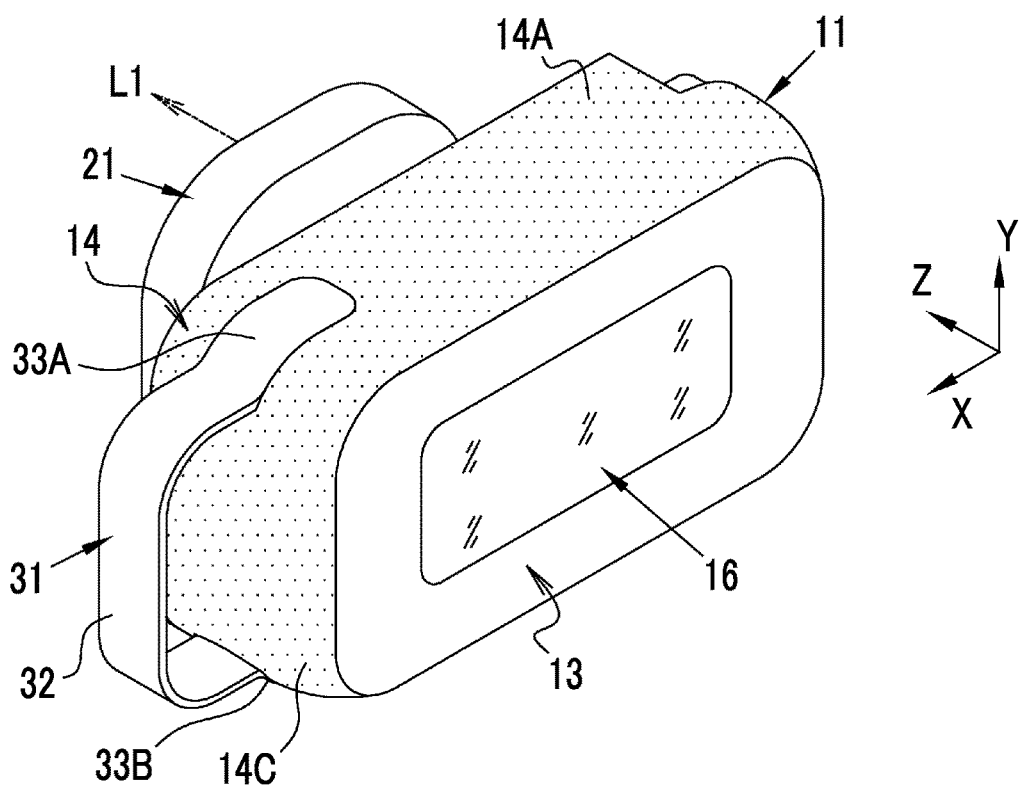
FIG. 2 is a perspective view of the X-ray tube device.

As shown in FIGS. 1 and 2, an X-ray tube device 10 comprises a main body 11, a collimator 21, a gripping portion 31, a switch 41, and the like.

The main body 11 incorporates a mono-tank 17 (see FIG. 3) including a bulb, which generates at least X-rays. In the embodiment, the main body 11 has a substantially rectangular parallelepiped shape. The substantially "rectangular parallelepiped shape" refers to that an appearance is formed by three sets of planes substantially parallel to each other, and the surfaces of the respective sets are substantially connected at 90 degrees. The substantially "rectangular parallelepiped shape" includes a case where connection portions of the surfaces of the respective sets are chamfered or the surfaces of the respective sets are connected with curved surfaces.

Hereinafter, an irradiation direction L1 of the X-rays in the X-ray tube device 10 is referred to as a Z direction, a longitudinal direction of the main body 11 that is a direction substantially perpendicular to the Z direction is referred to as an X direction, and a transverse direction of the main body 11 that is a direction substantially perpendicular to the Z direction and the X direction is referred to as a Y direction. The irradiation direction L1 of the X-rays in which a test object (not shown) is disposed is a positive direction of the Z direction, a side on which the gripping portion 31 is provided along the longitudinal direction of the main body 11 is a positive direction of the X direction, and a positive direction of the Y direction is determined such that the X direction, the Y direction, and the Z direction constitute a so-called right-handed system.

A surface facing the test object among the surfaces of the main body 11, that is, a surface in which the collimator 21 is provided is a front surface 12 of the main body 11. Accordingly, among the surfaces of the main body 11, the front surface 12 is a surface for irradiating the X-rays. Then, among the surfaces of the main body 11, a surface that faces the front surface 12 and is substantially parallel to the front surface 12 is a rear surface 13 of the main body 11. In the rear surface 13, an operating unit 16 that is used for setting, operation, and the like of the X-ray tube device 10 is provided (see FIG. 2). In the embodiment, although the operating unit 16 is a touch panel, the operating unit 16 can be constituted using at least one of buttons, switches, a display, or the like.

Among the surfaces of the main body 11, a surface that connects the front surface 12 and the rear surface 13 is a side surface 14 of the main body 11. That is, a surface excluding the front surface 12 and the rear surface 13 among the surfaces of the main body 11 is the side surface 14. In a case where the main body 11 is a substantially rectangular parallelepiped, the side surface 14 has an upper surface 14A and a lower surface 14B that face each other and are substantially parallel to each other, and a right surface 14C and a left surface 14D that face each other and are substantially parallel to each other.

The upper surface 14A is a portion in the side surface 14 that is visible in a case where the X-ray tube device 10 is viewed from a positive side in the Y direction. The lower surface 14B is a portion in the side surface 14 that is visible in a case where the X-ray tube device 10 is viewed from a negative side in the Y direction. The right surface 14C is a portion in the side surface 14 that is visible in a case where the X-ray tube device 10 is viewed from a positive side in the X direction. Similarly, the left surface 14D is a portion in the side surface 14 that is visible in a case where the X-ray tube device 10 is viewed from a negative side in the X direction. Accordingly, the upper surface 14A may partially overlap at least one of the right surface 14C or the left surface 14D. Similarly, the lower surface 14B may partially overlap at least one of the right surface 14C or the left surface 14D. The right surface 14C may partially overlap at least one of the upper surface 14A or the lower surface 14B, and the left surface 14D may partially overlap at least one of the upper surface 14A or the lower surface 14B. In the definition of each surface, it is assumed that a portion of the collimator 21 or the like hidden by a portion protruding from the main body 11 is included in the "visible portion".

Figure 3:
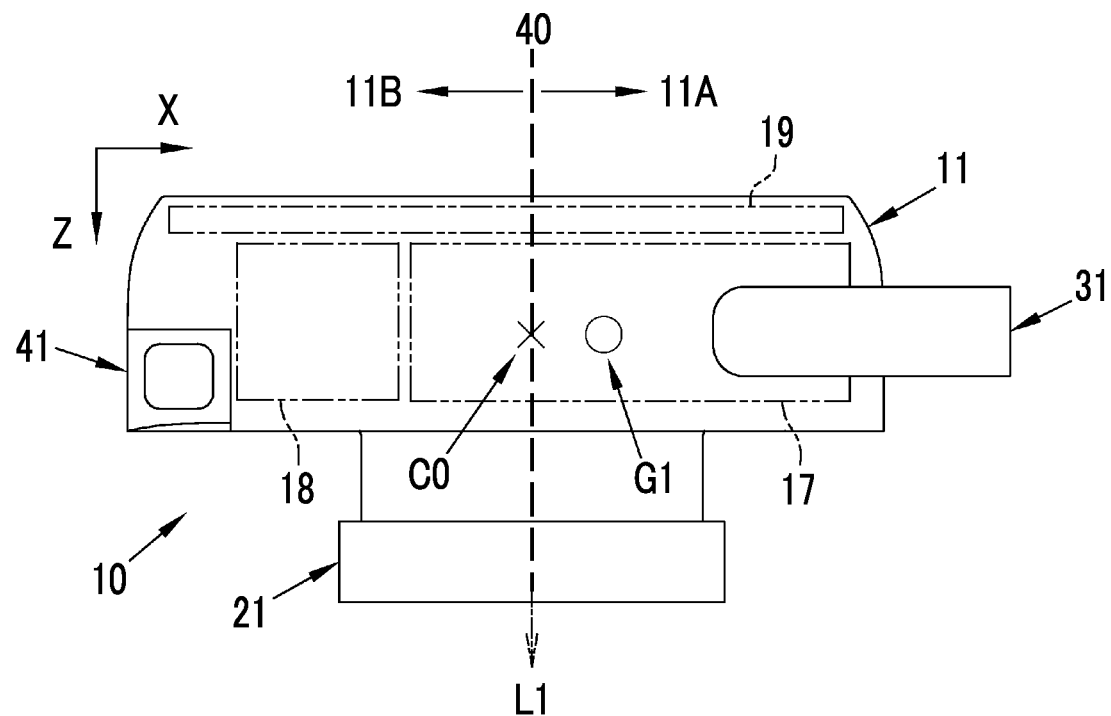
FIG. 3 is an explanatory view showing incorporated parts of a main body and positions of the center and the center of gravity of the main body.

As shown in FIG. 3, the main body 11 of the embodiment incorporates the mono-tank 17. The mono-tank 17 is an X-ray tube in which a bulb (not shown), which generates the X-rays, a high-voltage generation circuit (not shown) for operating the bulb, and the like are integrated. In the embodiment, although the mono-tank 17 is used, the main body 11 can incorporate parts constituting the mono-tank 17, such as the bulb and the high-voltage generation circuit, independently, instead of the mono-tank 17. In this case, the whole of the bulb, the high-voltage generation circuit, and the like being not integrated correspond to the mono-tank 17 of the embodiment.

The main body 11 incorporates a battery 18, a control circuit 19, and the like, in addition to the mono-tank 17 that generates the X-rays. The battery 18 supplies electric power necessary for operation to the mono-tank 17, the control circuit 19, and the like. The control circuit 19 controls the operation of the main body 11. That is, the control circuit 19 controls a tube voltage, a tube current, an X-ray generation (irradiation) timing, and the like of the mono-tank 17. The main body 11 can be provided with a plug, a cord, and the like that are connected to a power supply (not shown), which supplies electric power to the respective units of the main body 11, instead of the battery 18 or in addition to mounting of the battery 18. Although the mono-tank 17 is an X-ray tube that generates the X-rays, the main body 11 can be mounted with a bulb that generates radiation other than the X-rays, instead of the mono-tank 17 that is the X-ray tube. In this case, the X-ray tube device 10 constitutes a so-called radiation generation device according to the kind of radiation generated by the bulb.

Figure 4:
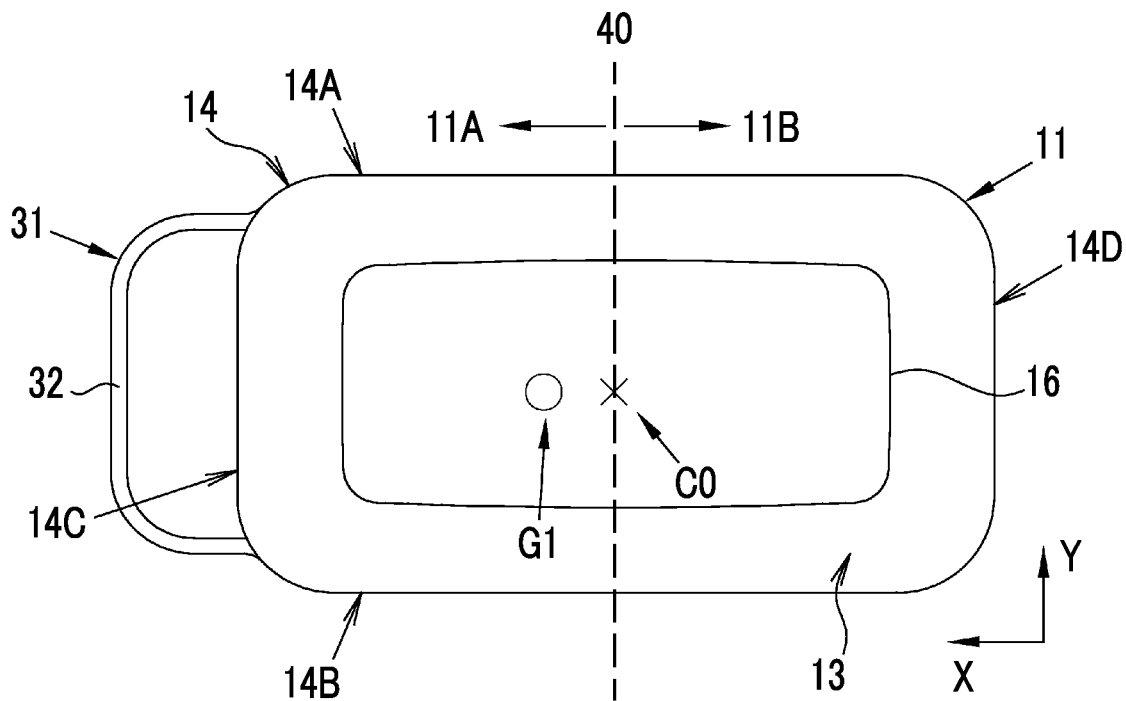
FIG. 4 is an explanatory view showing the center and the center of gravity of the main body.

Hereinafter, in a case where the main body 11 is divided into two portions of a portion including the center of gravity G1 (in the drawing, indicated by a mark "o") of the main body 11 and a portion not including the center of gravity G1 of the main body 11 using a plane 40 passing through the center C0 (in the drawing, indicated by a mark "x") of the main body 11 and the irradiation direction L1 of the X-rays, the portion including the center of gravity G1 of the main body 11 is referred to as a center-of-gravity-side portion 11A, and the portion not including the center of gravity G1 of the main body 11 is referred to as a non-center-of-gravity-side portion 11B. The center C0 of the main body 11 is a geometrical center of the main body 11. In the embodiment, a point where a distance from the front surface 12 is equal to a distance from the rear surface 13, a distance from the upper surface 14A is equal to a distance from the lower surface 14B, and a distance from the right surface 14C is equal to a distance from the left surface 14D is the center C0 of the main body 11. The center of gravity of the main body 11 is a center of gravity including not only a housing forming the main body 11 but also incorporated parts, such as the mono-tank 17. As shown in FIGS. 3 and 4, in the embodiment, the center of gravity G1 of the main body 11 is at a position shifted from the center C0 of the main body 11 to the right surface 14C.

The collimator 21 is provided to protrude from the main body 11 in the irradiation direction L1 (Z direction) of the X-rays in a part of the front surface 12, which is a surface of the main body 11, and has an irradiation window 23 for irradiating the X-rays with an adjusted irradiation range. The reason that the collimator 21 is formed in a shape protruding in "a part" of the front surface 12 of the main body 11 is to reduce the size, such as the appearance and volume of the X-ray tube device 10. In a case where the entire front surface 12 of the main body 11 protrudes and the main body 11 is in a shape in which the collimator 21 is included inside the main body 11, the entire volume of the main body 11, consequently, the X-ray tube device 10 increases. The irradiation range of the X-rays is a shape of the X-rays that reach an X-ray imaging panel or the like, an area of the X-rays, a position of the X-rays with respect to the X-ray tube device 10, and the like. While the X-rays generated by the mono-tank 17 are cone beams that spread in a conical shape, an imaging surface of the X-ray imaging panel generally has a rectangular shape. For this reason, the collimator 21 adjusts, for example, the cone beams generated by the mono-tank 17 in a quadrangular pyramid shape in conformity with the imaging surface of the X-ray imaging panel and irradiates the cone beams from the irradiation window 23. As a result, the collimator 21 suppresses wasteful exposure of the test object. The irradiation window 23 is formed of a material that can transmit at least the X-rays without waste. A surface where the irradiation window 23 is provided is a front surface 22 of the collimator 21. The collimator 21 incorporates one or a plurality of X-ray shielding members (not shown) and comprises an operating unit (not shown) that adjusts the internal arrangement (an inclination and the like) of the X-ray shielding members in order to adjust the irradiation range of the X-rays.

In a case where the portion of the collimator 21 is reduced in size in order to reduce the size of the entire X-ray tube device 10, the collimator 21 has a base end portion 21A having a diameter smaller than a distal end portion. The base end portion 21A of the collimator 21 is a portion on the front surface 12 side of the main body 11, and the distal end portion of the collimator 21 is a portion on the test object side. The reason that the collimator 21 is formed in the above-described shape in a case of reducing the size of the collimator 21 is because the X-rays spread in the irradiation direction L1.

The gripping portion 31 is provided to protrude from the main body 11 in the side surface 14, and is a handle that supports the main body 11 (and the entire X-ray tube device 10) by gripping. Only one gripping portion 31 is provided on the right surface 14C side of the main body 11. That is, the X-ray tube device 10 has the gripping portion 31 in the center-of-gravity-side portion 11A, and does not have the gripping portion 31 in the non-center-of-gravity-side portion 11B. The position, the orientation, and the like of the gripping portion 31 are fixed with respect to the main body 11. That is, the gripping portion 31 is unmovable. This is because, not only in carrying the X-ray tube device 10, but also in irradiating the X-rays from the X-ray tube device 10, a user grips and uses the gripping portion 31 to keep the posture of the X-ray tube device 10. The user can support the main body 11 in a posture necessary for imaging and can easily keep the posture even with one hand by gripping one gripping portion 31.

The gripping portion 31 is connected to the main body 11 at one place or two places. In the embodiment, the gripping portion 31 is connected to the main body 11 at two places of a connection point 33A and a connection point 33B. For this reason, the gripping portion 31 and the right surface 14C that is the side surface 14 of the main body 11 form a loop shape. The connection point 33A is a connection point to at least one of the upper surface 14A or the right surface 14C of the main body 11. The connection point 33B is a connection point to at least one of the lower surface 14B or the right surface 14C of the main body 11.

In the gripping portion 31, a flat plate portion 32 that is present between the connection point 33A and the connection point 33B is a standard gripping position. Unless there is a need to keep the X-ray tube device 10 in a special posture, normally, the user can easily support the posture of the X-ray tube device 10 in a posture necessary for imaging by gripping the flat plate portion 32. In the embodiment, although the flat plate portion 32 is a flat plate shape, the flat plate portion 32 may be formed in any shape. The flat plate portion 32 can be formed, for example, in a curved or more stereoscopic grip shape.

The switch 41 inputs at least one of an irradiation preparation instruction of the X-rays or an irradiation start instruction of the X-rays to the X-ray tube device 10. In the embodiment, the switch 41 is attachably and detachably provided in a corner portion of the main body 11 at a left end (an end on the negative side in the X direction) of the front surface 12 of the main body 11 and an end of the left surface 14D on the front surface 12 side, that is, at a corner of the non-center-of-gravity-side portion 11B on the front surface 12 side. The switch 41 is connected to the main body 11 in a wired or wireless manner, and can input the irradiation start instruction or the like and can transmit and receive other control signals even in a state in which the switch 41 is detached from the main body 11 as well as in a state in which the switch 41 is attached to the main body 11. Furthermore, the switch 41 can transmit or receive a synchronization signal to or from the X-ray imaging panel through the main body 11 or directly and can synchronously control the X-ray tube device 10 and the X-ray imaging panel. Synchronization regarding the operation includes a case where the operation is performed with a delay of a specific time.

The switch 41 comprises a support 42, and a button 43 that can perform a press operation. In a case where the switch 41 is attached to the main body 11, a surface of the support 42 is smoothly connected to the surface of the main body 11, such as the front surface 12 and the left surface 14D. For this reason, the switch 41 is integrated with the main body 11. On the other hand, in a case where the switch 41 is detached from the main body 11, the support 42 is a gripping portion that is used for gripping the switch 41. The button 43 is pressed in a case of inputting the irradiation start instruction or the like to the main body 11. The button 43 can perform, for example, a two-step press operation of a first step of a press operation to input the irradiation preparation instruction of the X-rays to the main body 11 and a second step of a press operation to input the irradiation start instruction in order to actually irradiates the X-rays after irradiation of the X-rays is enabled.

As described above, while the number of gripping portions 31 of the X-ray tube device 10 is one, one gripping portion 31 is in the center-of-gravity-side portion 11A including the center of gravity G1 of the main body 11. For this reason, not only in a case where the gripping portion 31 is gripped with both hands, but also in a case where the gripping portion 31 is gripped with one hand, it is possible to easily keep the posture of the main body 11, consequently, the X-ray tube device 10. This is because the gripping portion 31 is in the center-of-gravity-side portion 11A, such that the distance between the gripping portion 31 and the center of gravity G1 is small compared to a case where the gripping portion 31 is only in the non-center-of-gravity-side portion 11B; thus, force (for example, resistance to angular moment in an XY in-plane direction around the gripping position) necessary for keeping the posture of the main body 11 horizontally (a posture in which the upper surface 14A and the lower surface 14B are made horizontal) or the like is small. Even compared to a case where the center of gravity G1 of the main body 11 is at the center C0 of the main body 11, the X-ray tube device 10 requires small force to keep the posture of the main body 11. This is because a distance between the gripping portion 31 and the center of gravity G1 of the main body 11 is smaller than the distance between the gripping portion 31 and the center C0 of the main body 11. Accordingly, the X-ray tube device 10 is easily supported compared to an X-ray tube device in which the center of gravity G1 of the main body 11 is at the center C0 of the main body 11.

Figure 5:
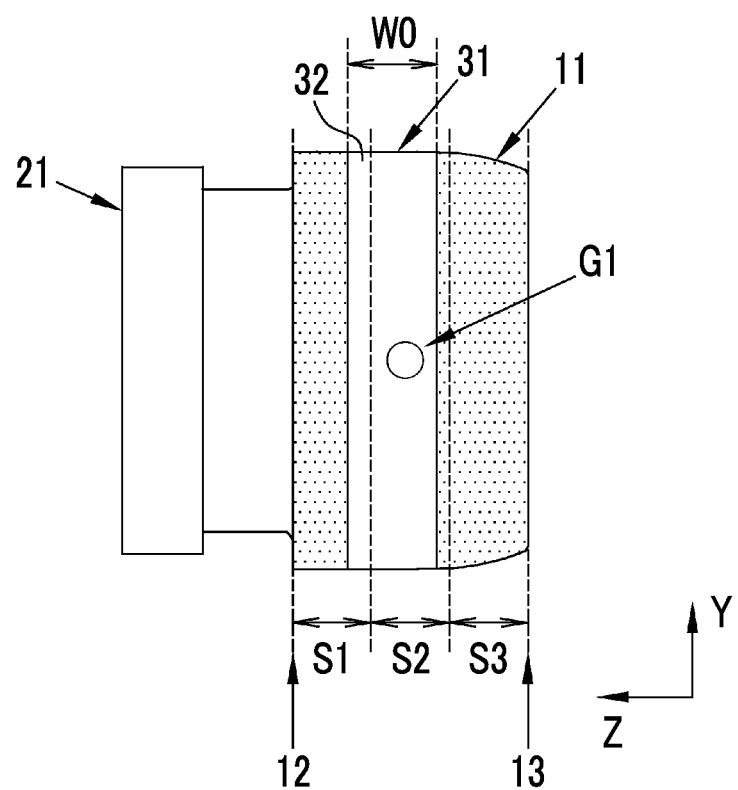
FIG. 5 is an explanatory view showing the position of the center of gravity of the main body.

As described above, in a case where one gripping portion 31 is provided only in the center-of-gravity-side portion 11A between the center-of-gravity-side portion 11A and the non-center-of-gravity-side portion 11B, it is preferable that the center of gravity G1 of the main body 11 is at the center between the front surface 12 and the rear surface 13. This is because, in a case where the posture of the X-ray tube device 10 is kept by gripping of the gripping portion 31, resistance to front-rear angular moment (angular moment in a YZ in-plane direction) of the X-ray tube device 10 is small compared to a case where the center of gravity G1 of the main body 11 is off-centered to the front surface 12 side or the rear surface 13 side. The condition that the center of gravity G1 of the main body 11 is "at the center" means that, as shown in FIG. 5, in a case where the main body 11 is equally sliced into three portions between the front surface 12 and the rear surface 13, and the three portions are represented as an S1 layer, an S2 layer, and an S3 layer in order from the front surface 12 side, the center of gravity G1 of the main body 11 is included in the S2 layer. A condition that the center of gravity G1 of the main body 11 is "on the front surface 12 side" means that the center of gravity G1 of the main body 11 is included in the S1 layer, and a condition that the center of gravity G1 of the main body 11 is "on the rear surface 13 side" means that the center of gravity G1 of the main body 11 is included in the S3 layer.

The center of gravity G1 of the main body 11 may be within a range of a width W0 of a flat plate portion 32 of the gripping portion 31 in a case where the X-ray tube device 10 is viewed from the negative side in the X direction. This is because the resistance to the front-rear angular moment of the X-ray tube device 10 is small compared to a case where the center of gravity G1 of the main body 11 is outside the range of the width W0 of the flat plate portion 32.

Second Embodiment

In the above-described first embodiment, although the position of the one gripping portion 31 is determined with the center of gravity G1 of the main body 11 as a reference, the position of the gripping portion 31 may be determined with the center of gravity G2 (see FIG. 6: indicated by a mark "•") of the mono-tank 17 as a reference, instead of the center of gravity G1 of the main body 11. That is, the X-ray tube device 10 can have a configuration in which, in a case where the main body 11 is divided into two portions of a center-of-gravity-side portion 11A including the center of gravity G2 of the mono-tank 17 and a non-center-of-gravity-side portion 11B not including the center of gravity G2 of the mono-tank 17 using the plane 40 passing through the center C0 of the main body 11 and the irradiation direction L1 of the X-rays, the gripping portion 31 is in the center-of-gravity-side portion 11A, and the gripping portion 31 is not in the non-center-of-gravity-side portion 11B. In a case where the main body 11 includes an individual bulb, an individual high-voltage generation circuit, and the like, instead of the mono-tank 17, the center of gravity of the whole of the elements constituting the mono-tank 17 is "the center of gravity G2 of the mono-tank 17" in the embodiment.

Figure 6:
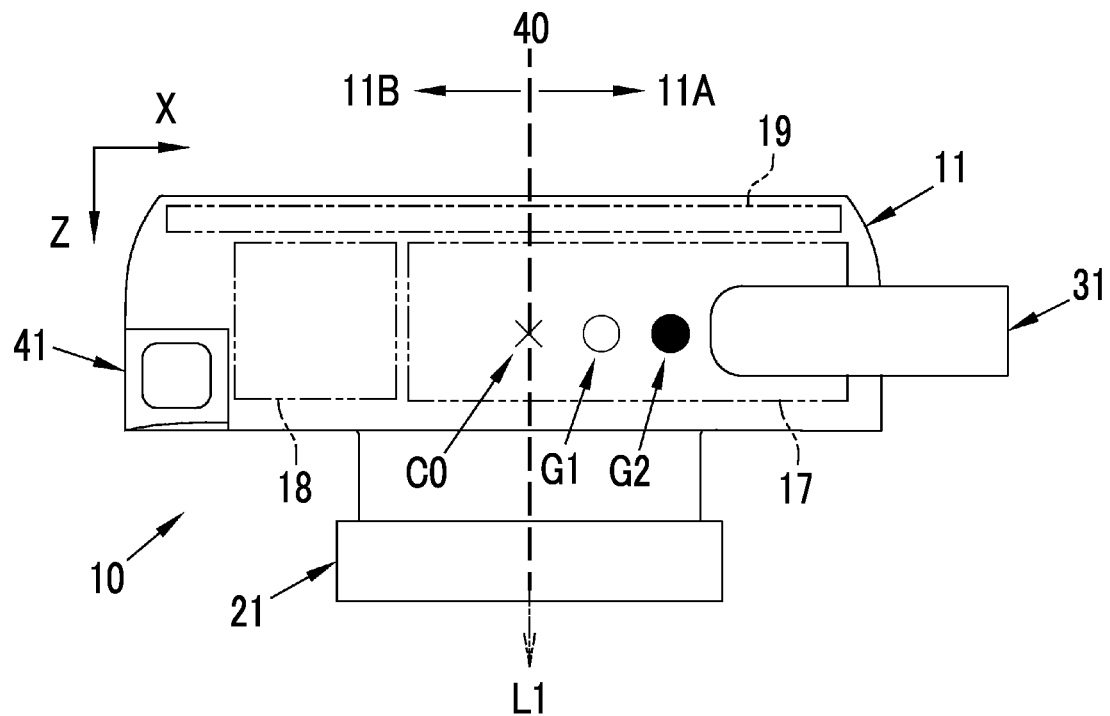
FIG. 6 is an explanatory view showing the center of the main body, the center of gravity of the main body, and the center of gravity of the mono-tank.

Since the mono-tank 17 is normally a heaviest part among the incorporated parts of the main body 11, normally, as shown in FIG. 6, the center of gravity G2 of the mono-tank 17 and the center of gravity G1 of the main body 11 are not so far from each other. For this reason, except for a case where the center of gravity G1 of the main body 11 and the center of gravity G2 of the mono-tank 17 are substantially at the center C0 of the main body 11, there is hardly a possibility that the center-of-gravity-side portion 11A and the non-center-of-gravity-side portion 11B determined with the center of gravity G2 of the mono-tank 17 as a reference are different from the center-of-gravity-side portion 11A and the non-center-of-gravity-side portion 11B determined with the center of gravity G1 of the main body 11 as a reference. Accordingly, even though the center of gravity G2 of the mono-tank 17 is used as a reference, the substantially same functional effects as in a case where the center of gravity G1 of the main body 11 is used as a reference are obtained.

As described above, in a case where one gripping portion 31 is provided only in the center-of-gravity-side portion 11A between the center-of-gravity-side portion 11A and the non-center-of-gravity-side portion 11B determined using the position of the center of gravity G2 of the mono-tank 17, it is preferable that the center of gravity G2 of the mono-tank 17 is at the center between the front surface 12 and the rear surface 13. The condition that the center of gravity G2 of the mono-tank 17 is "at the center" means that, as in the first embodiment, in a case where the main body 11 is equally sliced into three portions between the front surface 12 and the rear surface 13, and the three portions are represented as an S1 layer, an S2 layer, and an S3 layer in order from the front surface 12 side (see FIG. 5), the center of gravity G2 of the mono-tank 17 is included in the S2 layer. The center of gravity G2 of the mono-tank 17 may be within the range of the width W0 of the flat plate portion 32 of the gripping portion 31 in a case where the X-ray tube device 10 is viewed from the negative side in the X direction. The reasons and operations are the same as in the first embodiment.

Figure 7:
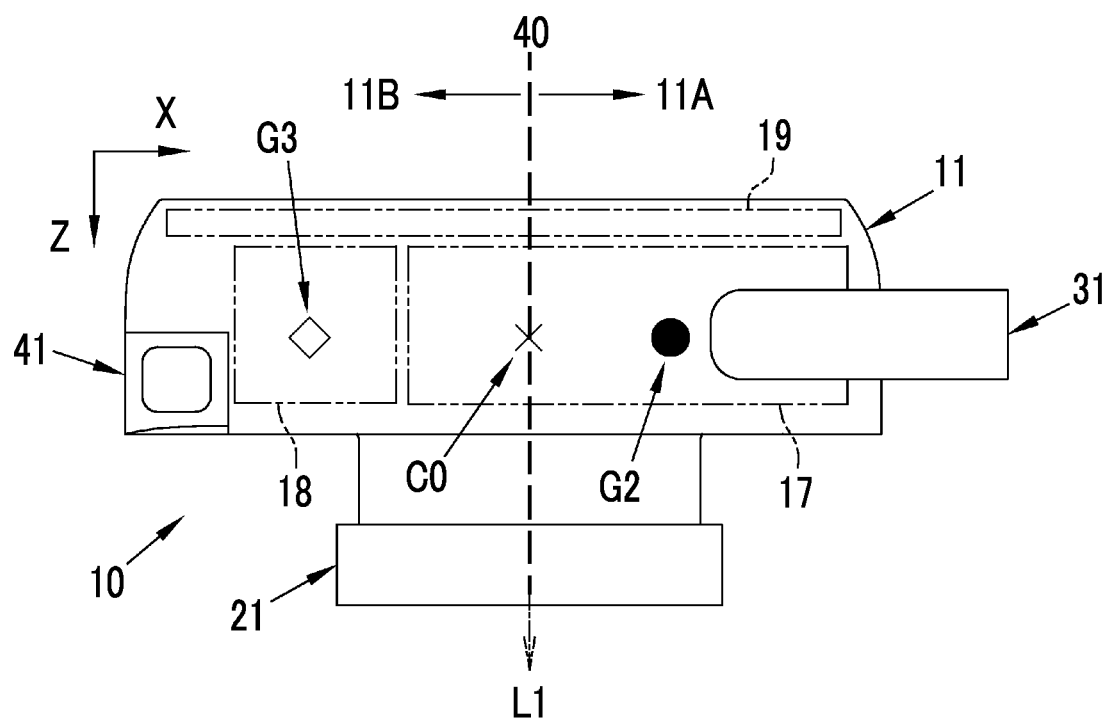
FIG. 7 is an explanatory view showing the positions of the center of the main body, the center of gravity of the mono-tank, and the center of gravity of the battery.

As described above, in a case where one gripping portion 31 is provided only in the center-of-gravity-side portion 11A between the center-of-gravity-side portion 11A and the non-center-of-gravity-side portion 11B determined using the position of the center of gravity G2 of the mono-tank 17, and as shown in FIG. 7, in a case where the main body 11 includes the battery 18, it is preferable that the center of gravity G3 of the battery 18 is in the non-center-of-gravity-side portion 11B. This is to prevent the center of gravity G1 of the main body 11 from being extremely off-centered due to mounting of the battery 18 since the battery 18 is the second heaviest part after the mono-tank 17 in a case where the battery 18 is mounted in the main body 11. This is because the center of gravity G3 of the battery 18 is in the center-of-gravity-side portion 11A, and a difference between the center of gravity imagined from the appearance of the main body 11 and the actual center of gravity G1 of the main body 11 becomes excessively large and there is a difficulty in using. As in the first embodiment, it is preferable the center of gravity G3 of the battery 18 is in the non-center-of-gravity-side portion 11B. That is, in a case where one gripping portion 31 is provided only in the center-of-gravity-side portion 11A between the center-of-gravity-side portion 11A and the non-center-of-gravity-side portion 11B using the center of gravity G1 of the main body 11, and in a case where the main body 11 includes the battery 18 (see FIG. 3), it is preferable that the center of gravity G3 of the battery 18 is in the non-center-of-gravity-side portion 11B.

Figure 8:
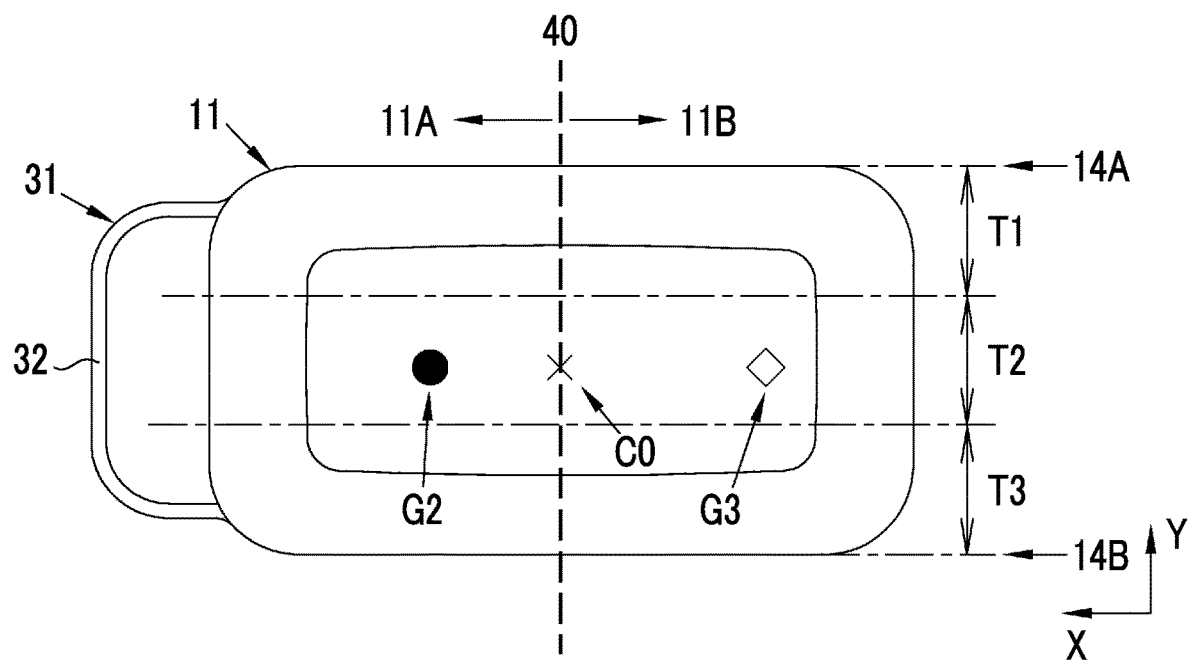
FIG. 8 is an explanatory view showing the positions of the center of the main body, the center of gravity of the mono-tank, and the center of gravity of the battery.

It is preferable that the center of gravity G2 of the mono-tank 17, the center C0 of the main body 11, and the center of gravity G3 (in the drawing, indicated by a mark "0") of the battery 18 are within the same layer. The condition that the center of gravity G2 of the mono-tank 17, the center C0 of the main body 11, and the center of gravity G3 of the battery 18 are "within the same layer" means that, as shown in FIG. 8, in a case where the main body 11 is equally sliced into three portions between the upper surface 14A and the lower surface 14B, and the three portions are represented as a T1 layer, a T2 layer, and a T3 layer in order from the upper surface 14A side, the center of gravity G2 of the mono-tank 17, the center C0 of the main body 11, and the center of gravity G3 of the battery 18 are included in the T2 layer. This is because, in a case where the center of gravity G2 of the mono-tank 17, the center C0 of the main body 11, and the center of gravity G3 of the battery 18 are within the same layer, in keeping the posture of the X-ray tube device 10 by gripping of the gripping portion 31, resistance to right-left angular moment (angular moment in an XY in-plane direction) of the X-ray tube device 10 is small compared to a case where any one of the center of gravity G2 and the center of gravity G3 is off-centered to the upper surface 14A side or the lower surface 14B side. Even in the first embodiment in which the center-of-gravity-side portion 11A and the non-center-of-gravity-side portion 11B are determined with the center of gravity G1 of the main body 11 as a reference, it is preferable that the center of gravity G2 of the mono-tank 17, the center C0 of the main body 11, and the center of gravity G3 of the battery 18 are within the same layer.

Figure 9:
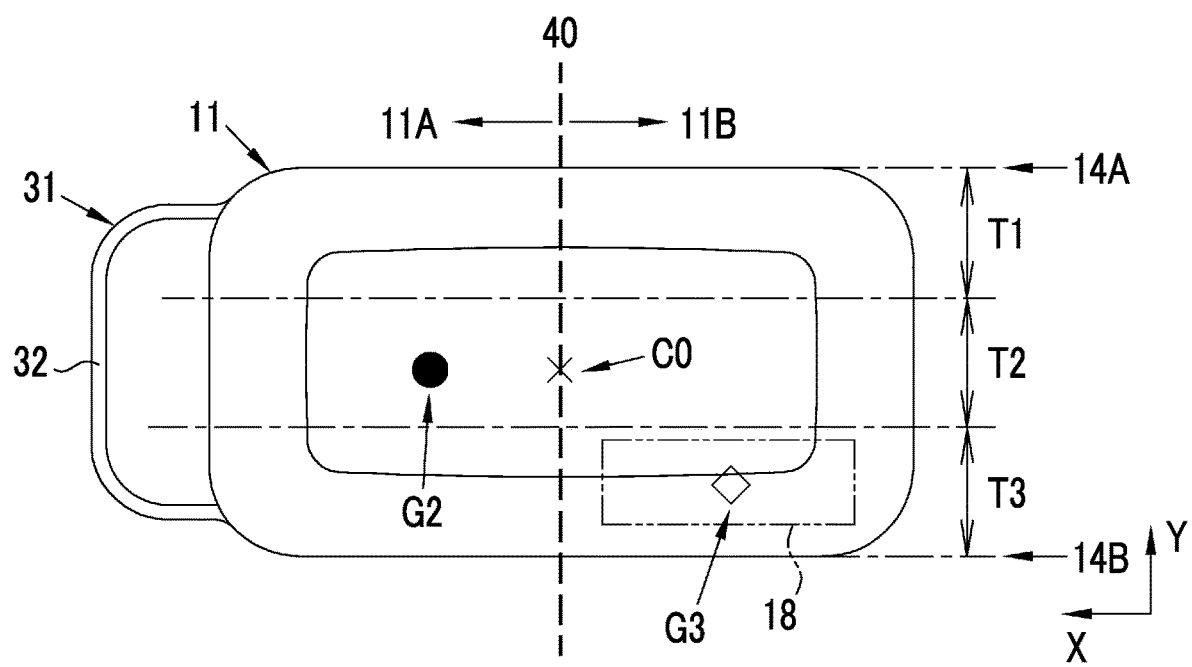
FIG. 9 is an explanatory view showing the positions of the center of the main body, the center of gravity of the mono-tank, and the center of gravity of the battery.

In a case where the battery 18 is small and is lightweight with respect to the mono-tank 17, as shown in FIG. 9, even in a case where one gripping portion 31 is provided only in the center-of-gravity-side portion 11A between the center-of-gravity-side portion 11A and the non-center-of-gravity-side portion 11B determined using the position of the center of gravity G2 of the mono-tank 17, the center of gravity G3 of the battery 18 may be in, for example, the T3 layer. This is because, in a case where the battery 18 is lightweight with respect to the mono-tank 17, even though the center of gravity G3 of the battery 18 is neglected, in a case where the center of gravity G1 of the main body 11 and the center of gravity G2 of the mono-tank 17 are at the substantially same position, angular moment in the right-left direction of the battery 18 in gripping the gripping portion 31 is negligible.

In the first embodiment and the second embodiment described above, although the gripping portion 31 is connected to the main body 11 at two places of a connection point 33A and a connection point 33B and the gripping portion 31 and the side surface 14 of the main body 11 form the loop shape, the gripping portion 31 having the shape easily prevents dropping of the X-ray tube device 10. This is because, even though the user almost releases the gripping portion 31 by mistake, the hand is caught by the loop shape.

Figure 10:
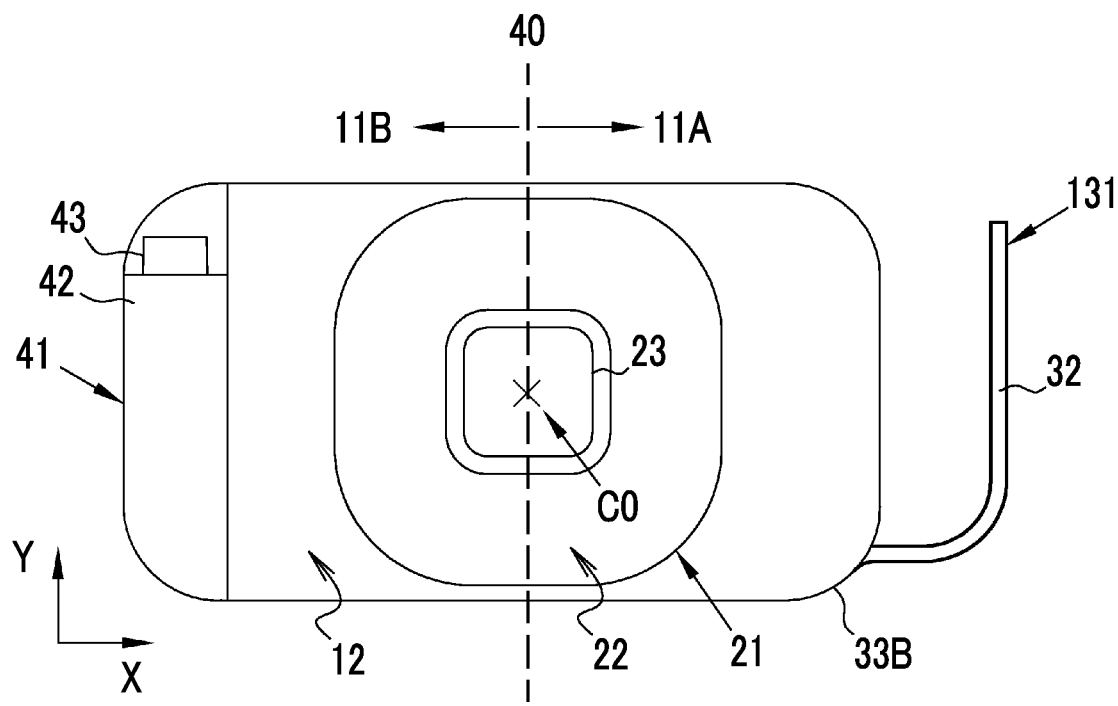
FIG. 10 is a front view of an X-ray tube device having an L-shaped gripping portion.

Instead of the gripping portion 31 of the first embodiment and the second embodiment described above, as shown in FIG. 10, an L-shaped gripping portion 131 in which the flat plate portion 32 is connected to the main body 11 at one place of the connection point 33B, and the other end of the flat plate portion 32 is not connected to the main body 11 may be provided. The L-shaped gripping portion 131 allows the X-ray tube device 10 placed on an examination table or the like to be easily lifted up, and allows the gripped X-ray tube device 10 to be easily placed on the examination table or the like. This is because the upper surface 14A side is opened; thus, the hand is not caught by the gripping portion 131.

Figure 11:
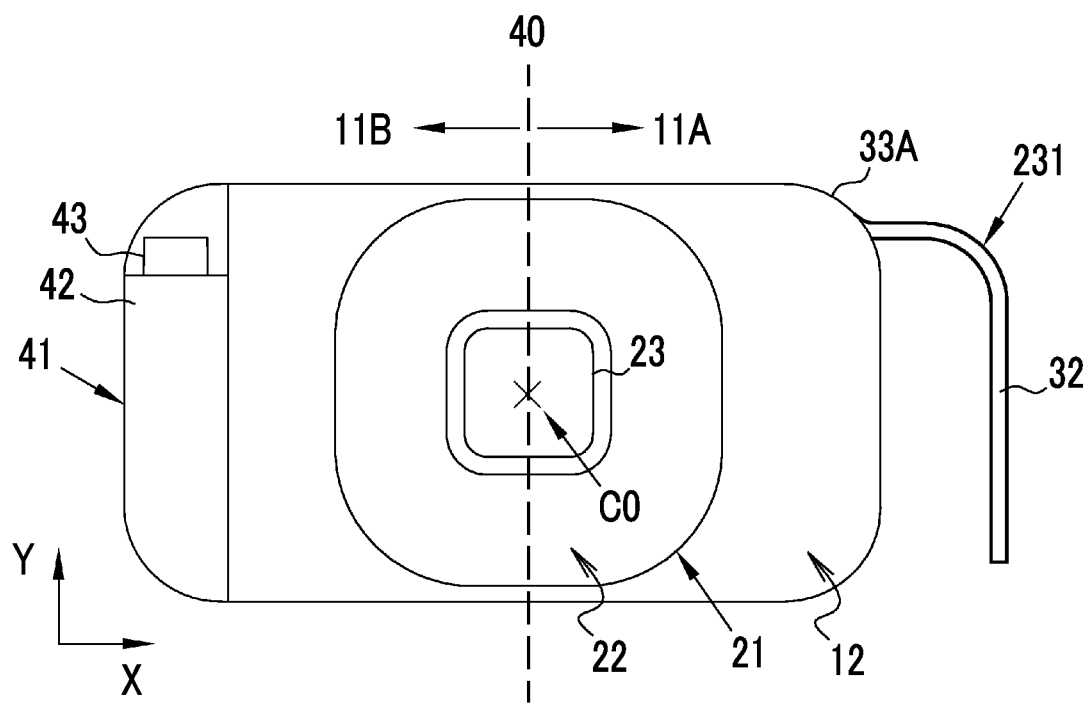
FIG. 11 is a front view of an X-ray tube device having an inverted L-shaped gripping portion.

Instead of the gripping portion 31 of the first embodiment and the second embodiment described above, as shown in FIG. 11, an inverted L-shaped gripping portion 231 in which the flat plate portion 32 is connected to the main body 11 at one place of the connection point 33A, and the other end of the flat plate portion 32 is not connected to the main body 11 may be provided. In a case where the X-ray tube device 10 is used in a regular posture (a posture in which the positive side in the Y direction is directed vertically upward, the inverted L-shaped gripping portion 231 easily prevents dropping, allows the X-ray tube device 10 placed on the examination table or the like to be easily lifted up, and allows the gripped X-ray tube device 10 to be easily placed on the examination table or the like). This is because the upper surface 14A side is closed and the lower surface 14B side is opened.

In the first embodiment and the second embodiment described above, although the switch 41 is provided in the non-center-of-gravity-side portion 11B, and this is to allow the user to operate the switch 41 with a hand opposite to a hand gripping the gripping portion 31 (or the gripping portion 131 or the gripping portion 231 of the above-described modification example; the same applies to the following.). In this way, in a case where the switch 41 is provided in the non-center-of-gravity-side portion 11B, the user can use the X-ray tube device 10 with a sense of use similar to a familiar imaging apparatus, such as a digital camera. For this reason, an irradiation position and the like of the X-rays can be easily and finely adjusted compared to the X-ray tube device of the related art according to the proficiency or the like of the user.

As in the first embodiment and the second embodiment described above, in a case where the main body 11 has a rectangular parallelepiped shape, and the front surface 12 and the rear surface 13 of the main body 11 have a rectangular shape, it is preferable that the gripping portion 31 in the side surface 14 (in the first embodiment and the second embodiment described above, the right surface 14C or the left surface 14D) of the main body 11 including short sides of the front surface 12 and the rear surface 13 of the main body 11. The reason is because, in a case where the gripping portion 31 is provided along the short sides of the front surface 12 and the rear surface 13, the flat plate portion 32 is relatively short; thus, a position in the flat plate portion 32 where the main body 11 is easily supported can be substantially automatically gripped compared to a case where the gripping portion 31 is provided along long sides of the front surface 12 and the rear surface 13.

EXPLANATION OF REFERENCES

10: X-ray tube device
11: main body

11A: center-of-gravity-side portion
11B: non-center-of-gravity-side portion
12: front surface
13: rear surface
14: side surface
14A: upper surface
14B: lower surface
14C: right surface
14D: left surface
16: operating unit
17: mono-tank
18: battery
19: control circuit
21: collimator
21A: base end portion
22: front surface
23: irradiation window
31, 131, 231: gripping portion
32: flat plate portion
33A, 33B: connection point
40: plane
41: switch
42: support
43: button
C0: center of main body
G1: center of gravity of main body
G2: center of gravity of ray tube
G3: center of gravity of battery
L1: irradiation direction of X-ray
S1, S2, S3, T1, T2, T3: layer
W0: width of gripping portion

What is claimed is:

1. An X-ray tube device comprising:
a main body that incorporates a mono-tank including a bulb, which generates X-rays, and has a front surface, which is a surface for irradiating the X-rays, a rear surface, which is a surface facing the front surface, and a side surface, which is a surface connecting the front surface and the rear surface; and
one gripping portion that is provided to protrude from the main body on the side surface and supports the main body by gripping,
wherein, in a case where the main body is divided into two portions of a center-of-gravity-side portion including a center of gravity of the main body and a non-center-of-gravity-side portion not including the center of gravity using a plane passing through a center of the main body and an irradiation direction of the X-rays, the gripping portion is in the center-of-gravity-side portion, and the gripping portion is not in the non-center-of-gravity-side portion,
wherein the one gripping portion is the only gripping portion that is provided to protrude from the main body and supports the main body by gripping.

2. The X-ray tube device according to claim 1,
wherein the center of gravity of the main body is at a center between the front surface and the rear surface.

3. The X-ray tube device according to claim 1,
wherein, in a case where the main body includes a battery, a center of gravity of the battery is in the non-center-of-gravity-side portion.

4. The X-ray tube device according to claim 2,
wherein, in a case where the main body includes a battery, a center of gravity of the battery is in the non-center-of-gravity-side portion.

5. The X-ray tube device according to claim 3,
wherein the center of gravity of the mono-tank, the center of the main body, and the center of gravity of the battery are within the same layer.

6. The X-ray tube device according to claim 1,
wherein the gripping portion is connected to the main body at one place or two places.

7. The X-ray tube device according to claim 1,
wherein the gripping portion and the side surface form a loop shape.

8. The X-ray tube device according to claim 1,
wherein a switch for instructing irradiation of the X-rays is in the non-center-of-gravity-side portion.

9. The X-ray tube device according to claim 3,
wherein a switch for instructing irradiation of the X-rays is in the non-center-of-gravity-side portion.

10. The X-ray tube device according to claim 1,
wherein, in a case where the front surface and the rear surface have a rectangular shape, the gripping portion is provided in the side surface of the main body including short sides of the front surface and the rear surface.

11. An X-ray tube device comprising:
a main body that incorporates a mono-tank including a bulb, which generates X-rays, and has a front surface, which is a surface for irradiating the X-rays, a rear surface, which is a surface facing the front surface, and a side surface, which is a surface connecting the front surface and the rear surface; and
one gripping portion that is provided to protrude from the main body on the side surface and supports the main body by gripping,
wherein, in a case where the main body is divided into two portions of a center-of-gravity-side portion including a center of gravity of the mono-tank and a non-center-of-gravity-side portion not including the center of gravity using a plane passing through a center of the main body and an irradiation direction of the X-rays, the gripping portion is in the center-of-gravity-side portion, and the gripping portion is not in the non-center-of-gravity-side portion,
wherein the one gripping portion is the only gripping portion that is provided to protrude from the main body and supports the main body by gripping.

12. The X-ray tube device according to claim 11,
wherein the center of gravity of the mono-tank is at a center between the front surface and the rear surface.

13. The X-ray tube device according to claim 11,
wherein, in a case where the main body includes a battery, a center of gravity of the battery is in the non-center-of-gravity-side portion.

14. The X-ray tube device according to claim 12,
wherein, in a case where the main body includes a battery, a center of gravity of the battery is in the non-center-of-gravity-side portion.

15. The X-ray tube device according to claim 13,
wherein the center of gravity of the mono-tank, the center of the main body, and the center of gravity of the battery are within the same layer.

16. The X-ray tube device according to claim 11,
wherein the gripping portion is connected to the main body at one place or two places.

17. The X-ray tube device according to claim 11,
wherein the gripping portion and the side surface form a loop shape.

18. The X-ray tube device according to claim 11,
wherein a switch for instructing irradiation of the X-rays is in the non-center-of-gravity-side portion.

19. The X-ray tube device according to claim 13, wherein a switch for instructing irradiation of the X-rays is in the non-center-of-gravity-side portion.

20. The X-ray tube device according to claim 11, wherein, in a case where the front surface and the rear surface have a rectangular shape, the gripping portion is provided in the side surface of the main body including short sides of the front surface and the rear surface.

* * * * *